US008221797B2

(12) United States Patent
Zhang et al.

(10) Patent No.: US 8,221,797 B2
(45) Date of Patent: Jul. 17, 2012

(54) WOOD PRESERVING COMPOSITION FOR TREATMENT OF IN-SERVICE POLES, POSTS, PILING, CROSS-TIES AND OTHER WOODED STRUCTURES

(75) Inventors: Jun Zhang, Getzville, NY (US); Douglas J. Herdman, Orchard Park, NY (US); Richard J. Ziobro, Peachtree City, GA (US)

(73) Assignee: Osmose, Inc., Buffalo, NY (US)

( * ) Notice: Subject to any disclaimer, the term of this patent is extended or adjusted under 35 U.S.C. 154(b) by 387 days.

(21) Appl. No.: 12/068,743

(22) Filed: Feb. 11, 2008

(65) Prior Publication Data

US 2008/0193640 A1 Aug. 14, 2008

Related U.S. Application Data

(60) Provisional application No. 60/889,153, filed on Feb. 9, 2007.

(51) Int. Cl.
*A01N 59/20* (2006.01)
*A61K 33/34* (2006.01)
*B05D 7/06* (2006.01)

(52) U.S. Cl. ........ 424/638; 424/630; 424/631; 424/632; 252/384; 252/385; 252/400.4; 252/400.53; 106/15.05; 106/18.3; 106/18.32

(58) Field of Classification Search ............... 106/15.05, 106/18.3, 18.32; 424/630, 631, 632, 638; 252/384, 385, 400.4, 400.53
See application file for complete search history.

(56) References Cited

U.S. PATENT DOCUMENTS 4,075,121 A * 2/1978 Konno et al. ................. 252/407
4,656,060 A * 4/1987 Krzyzewski .................. 427/397
5,084,280 A 1/1992 West
5,342,438 A 8/1994 West
5,977,168 A * 11/1999 Konishi et al. ................ 514/471
6,110,263 A 8/2000 Goettsche et al.
6,306,202 B1 10/2001 West
6,352,583 B1 3/2002 Goettsche et al.
7,238,654 B2 7/2007 Hodge et al.
7,252,706 B2 8/2007 Richardson et al.
7,316,738 B2 1/2008 Richardson et al.
2004/0258767 A1 12/2004 Leach et al.
2004/0258768 A1* 12/2004 Richardson et al. .......... 424/630
2005/0118280 A1 6/2005 Leach et al.
2005/0252408 A1* 11/2005 Richardson et al. ....... 106/15.05
2005/0255251 A1* 11/2005 Hodge et al. .................. 427/397
2006/0009535 A1* 1/2006 Wantling ...................... 516/43
2006/0062926 A1* 3/2006 Richardson et al. .......... 427/440
2006/0075923 A1 4/2006 Richardson et al.
2006/0086841 A1 4/2006 Richardson et al.
2006/0276468 A1* 12/2006 Blow ......................... 514/232.5
2006/0288904 A1 12/2006 Leach et al.
2007/0021385 A1* 1/2007 Zhang et al. .................... 514/63
2009/0004497 A1* 1/2009 Blow ......................... 428/537.1
2009/0223408 A1* 9/2009 Richardson et al. ......... 106/18.3
2009/0280185 A1* 11/2009 Richardson et al. .......... 424/489
2010/0068545 A1* 3/2010 Zhang et al. ............... 428/537.1

FOREIGN PATENT DOCUMENTS

WO WO 03/103392 A1 12/2003

OTHER PUBLICATIONS

Liu, Y. et al., Michigan Technical Univ. Dept. Chemistry, Houghton, MI, "Use of Polymeric Nanoparticles for controlled release of biocides in solid wood" Materials research society symposium proceedings series, 1998, vol. 550, abstract GG3.4.
Liu, Y. et al. "Use of Nanoparticles for the Controlled Release of Biocides in Pressure-treated Solid Wood" poltymer preprints 38(2), 1997, pp. 624-625.
Liu Y, "Use of polymer nanopartcles as carriers for the controlled release of biocides in solid wood" Ph.D. dissertation of Yong Liu, Michigan Technological University, Houghton, MI. 1999.
Liu, Y. et al. "Use of nanoparticles for controlled release of biocides in solid wood" journal of applied polymer science, vol. 79, 2001, pp. 458-465.
Lide, "Characteristics of particles and particle dispersoids" handbook of chemistry and physics, 75th edition, 1994, Florida, CRC press, p. 15-38.
Shaw, www.fad.gov/ohrms/dockets/ac/01/slides/3763s2_09_shaw.ppt; 2001.
Hawley's Condensed Chemical Dictionary, 14th edition, John Wiley & Sons, Inc. 2001, p. 86.
Superior Court of New Jersey, Decision after trial, *Phibrotech Inc.* v. *Osmose Holdings, Inc.* Jun. 25, 2007.
Superior Court of New Jersey Chancery Division, Final Judgment, *Phibrotech, Inc.* v. *Osmose Holdings, Inc. Osmose, Inc.* Aug. 14, 2007.
American Wood-preservers' Association Standard A3-05 (2005).
American Wood-preservers' Association Standard C1-03 (2003).

* cited by examiner

*Primary Examiner* — Joseph D Anthony
(74) *Attorney, Agent, or Firm* — Covington & Burling LLP; Einar Stole; Melody Wu

(57) ABSTRACT

This invention discloses a wood preservative composition for the supplemental or remedial treatment of in-service poles, posts, piling, cross ties and other wooden structures. The wood preservative composition comprises copper 8-hydroxyquinolate (oxine copper) in combination with a boron compound or a fluoride compound.

53 Claims, No Drawings

WOOD PRESERVING COMPOSITION FOR TREATMENT OF IN-SERVICE POLES, POSTS, PILING, CROSS-TIES AND OTHER WOODED STRUCTURES

This application claims benefit to U.S. Provisional Application Ser. No. 60/889,153, filed on Feb. 9, 2007.

FIELD OF INVENTION

This invention relates to wood preserving compositions for the supplemental or remedial treatment of wood in service, such as utility poles and railroad ties.

BACKGROUND OF INVENTION

Wood and/or cellulose based products exposed in an outdoor environment are biodegradable, primarily through attack by microorganisms. As a result, they will decay, weaken in strength, and discolor. The microorganisms causing wood deterioration include brown rots such as *Postia placenta, Gloeophyllum trabeum* and *Coniophora puteana*, white rots such as *Irpex lacteus* and *Trametes versicolor*, dry rots such as *Serpula lacrymans* and *Meruliporia incrassata* and soft rots such as *Cephalosporium, Acremonium*, and *Chaetomium*. In addition, wood is still subject to attack by wood-inhabiting insects, such as termites, beetles, ants, bees, wasps and so on. Wood preservatives are well known for preserving wood and extend the service life of wood products including decking boards, fence posts, utility poles, railroad ties, permanent wood foundation, and other cellulose-based materials, such as paper, plywood, particleboard, textiles, rope, etc., against organisms responsible for the deterioration of wood.

Utility poles and railroad cross ties are wooden structures that are traditionally pressure treated with wood preservative chemicals, such as chromated copper arsenate (CCA), pentachlorophenol, copper naphthanate or creosote. Pressure treatment with preserving chemicals can certainly prevent utility poles or railroad cross ties from fungal and termite attack and the pressure treatment can usually last for 30 to 40 years. However, the wood preserving chemicals can only penetrate through most of the sapwood portion of the wood species and rarely penetrate the heartwood portion. This will cause insufficient treatment and insufficient chemical absorption. In addition, improper treating practices may also cause poor treatment and insufficient chemical loadings. A direct consequence of the poor penetration and insufficient chemical loading is that, once the treated utility poles are placed in service, often times a small percentage of poles show early failure and subsequent strength loss. As a result, a supplemental or remedial treatment is needed to offer the protection for those poles that show early failures. In older poles, the preservative chemicals in the outer sapwood zone will gradually decline due to water leaching, ultraviolet degradation, chemical alteration or physical damage. As a result, external decay or termite attack may develop on the outer surface, and therefore there is an additional need for supplemental or remedial treatments to further extend the service life of aging utility poles and other wooden structures.

Preservative groundline treatments provide an economical extension to the useful life of utility poles. Experience has shown that groundline decay can be postponed almost indefinitely in cases where periodic inspection and maintenance programs are in effect. External treatments on utility poles and other wooden structures are typically applied below the ground level either as pastes or grease-type compositions that are brushed on the wood surface, and then covered with a moisture resistant barrier, or as self-contained ready-made preservative bandages. In both cases, the goal is to supplement the original preservative treatment to prevent or arrest surface decay. Protection is dependent upon the ability of the active ingredients to penetrate and remain in the treatment zone, and is limited to the depth of penetration. In addition, the composition must possess satisfactory physical properties, such as viscosity, spreadability, adherence, etc.

Historically, oilborne preservatives have been used for treating in-service utility poles and other wooden structures. Traditional oilborne preservatives included petroleum oils, creosote, copper naphthenate and pentachlorophenol. However, the use of oilborne supplemental preservatives is declining due to concerns of worker exposure to the organic solvents and leaching of the organic solvents into the environment. Furthermore, the organic solvents, including No. 2 fuel oil, have recently experienced unprecedented price increases making them cost prohibitive for the manufacture of supplemental/remedial wood preservative compositions.

Current, known commercially established preservatives for the after protection of in-service utility poles and other wooden structures contain copper or copper combined with boron and/or fluoride as their active biocides. Copper compounds, such as copper sulfate, copper carbonate and copper hydroxide, are generally known to be effective biocides as wood preservatives. Preferred copper compounds are generally insoluble and therefore must be solubilized to be effective in supplemental wood preservative compositions. This is typically accomplished by complexing the copper compounds with ammonia, acids or amines. Known copper complexes used in the field of wood preservation include copper naphthenate, water-dispersible copper naphthenate, copper ethanolamine, ammoniacal copper citrate, alkaline copper quaternary and others. Sodium fluoride and sodium borate are the most commonly used biocides in remedial preservative compositions. The sodium salts of boron and fluoride are able to penetrate further through the wood structure due to their water solubility and mobility.

Although prior art compositions for the remedial treatment of utility poles and other wooden structures have been shown to be effective in extending the useful life of wood products in-service, there are several problems that exist with current preservative compositions.

One limitation of using oil or water dilutable copper complexes is that they can readily leach from wood. Leaching of copper from wood can be further increased by the presence of oil solvents present in utility poles or cross ties from initial treatment with pentachlorophenol, creosote or copper naphthenate. Elevated moisture levels commonly found within in-service poles and ties, particularly near or below groundline, can also increase the leaching rate of water dilutable copper complexes found in current preservative paste compositions.

The leaching of the copper component from current paste compositions is a concern from both a performance and environmental perspective. Depletion of the copper by leaching will ultimately compromise the long term bioefficacy of the supplemental or remedial formulation, and the leached copper causes concern that the environment surrounding the treated structure will be contaminated. It has been established that copper is extremely toxic to fish and other aquatic organisms at very low concentrations. Concerns over copper leaching from supplemental wood preservative compositions are such that their use is often limited or even restricted in areas of standing water or near water ways.

In addition, the copper component of current supplemental wood preservative compositions is not protective against some species of copper-tolerant wood decay fungi, often located in the Gulf-Coast region of the U.S. Generally, higher loadings of copper are required in remedial compositions containing soluble forms of copper and/or a co-biocide is incorporated into the composition to afford protection against copper-tolerant decay fungi.

Another concern with current copper containing paste compositions is worker exposure when applying to in-service wooden structures. Copper complexes formed with the use of amines such as monoethanolamine, ethylenediamine and the like, acids such as, for example, naphthenic or arsenic acid and ammonia can be corrosive to human eyes and skin and may be fatal if ingested. As a result, personal protective equipment required by personnel applying current remedial compositions can be costly, cumbersome and may interfere with the correct application of the material to an in-service wooden structure.

Finally, complexing copper to impart solubility can be expensive. Generally, high levels of the complexing agents are required to solubilize copper compounds. For example, 2 to 4 moles of monoethanolamine are required to complex 1 mole of copper and 4 moles of ammonia are needed to complex 1 mole of copper. This can add considerable cost to the formulated remedial preservative compositions. In addition, oilborne copper naphthenate and other oil-based compositions generally require the use of No. 2 fuel oil as a carrier and are therefore extremely susceptible to large variations in cost.

Examples of supplemental or remedial preservative compositions for the afterprotection of wood in-service can be found in the following literature.

U.S. Pat. No. 5,342,438 to West discloses a non-water dilutable remedial wood preservative containing copper derived from an amine-inorganic copper complex, combined with at least one sodium salt selected from the group consisting of sodium borate and sodium fluoride in a ratio of 2 to 120 parts of the sodium salt for each part of copper in the preservative.

U.S. Pat. No. 6,110,263 to Goettsche teaches a process for the afterprotection of wood, which comprises treating the wood with and effective wood preserving amount of a wood preservative composition comprising a copper compound, a polyamine or alkanolamine having at least two nitrogen atoms, and an inorganic fungicide, the treatment being effected by means of a bandaging process, an inoculation injection process, a borehole process or a paste process.

U.S. Pat. No. 5,084,280 to West claims a paste composition for preserving wood which contains as its only active wood preservation ingredients a mixture of 10-90% by weight of a water-dispersible copper naphthenate and 90-10% by weight of borax.

U.S. Pat. No. 6,352,583 to Goettsche discloses a wood preservative for the supplemental protection of wood, consisting essentially of one or more copper compounds, one or more alkanolmonoamines and one or more complexing organic carboxylic acids or ammonium or alkali metal salts of said complexing organic carboxylic acids.

U.S. Pat. No. 6,306,202 to West teaches a water soluble fixed copper-borax wood preservative composition which comprises a fixed copper compound selected from the group consisting of copper oxides, copper hydroxide, basic copper carbonate, basic copper sulfate, and copper oxychloride combined in water with sodium tetraborate decahydrate wherein the fixed copper compound concentration ranges from 0.01 parts to 0.20 parts for each part of sodium tetraborate decahydrate.

This invention discloses a supplemental or remedial wood preservative composition which solves the problems identified with current, known compositions and addresses the need for a more environmentally friendly technology for the after-protection of in-service wooden structures. This need is solved by the subject matter disclosed herein.

SUMMARY OF THE INVENTION

The present invention provides a wood preservative composition comprising an organic biocide, a carrier, and a thickening agent, wherein the wood preservative composition is formulated as a thixotropic paste. In one embodiment, the organic biocide is a fungicide, insecticide, moldicide, bactericide, or algaecide, or combinations thereof. In a preferred embodiment, the organic biocide is a quaternary ammonium compound, a triazole compound, an imidazole compound, an isothiazolone compound, or a pyrethroid compound, or combination thereof. In another embodiment, the organic biocide is imidachloprid, fipronil, cyfluthrin, bifenthrin, permethrin, cypermethrin, chlorpyrifos, iodopropynyl butylcarbamate (IPBC), chlorothalonil, 2-(thiocyanatomethylthio) benzothiazole, alkoxylated diamines or carbendazim.

The present invention also provides a wood preservative composition comprising an organic biocide, copper-8-quinolinolate, a carrier, and a thickening agent, wherein the wood preservative composition is formulated as a thixotropic paste.

The present invention also provides a wood preservative composition comprising an organic biocide, a boron-containing compound, a carrier, and a thickening agent, wherein the wood preservative composition is formulated as a thixotropic paste. In a preferred embodiment, the boron-containing compound is a boric acid, a metal borate, a sodium borate, or a potassium borate. In one embodiment, the sodium borate is sodium tetraborate decahydrate, sodium tetraborate pentahydrate, or disodium octaborate tetrahydrate (DOT). In another embodiment, the metal borate is calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate or zinc borate.

The present invention teaches a supplemental or remedial wood preserving composition which comprises copper-8-quinolinolate (oxine copper) combined with at least one boron compound or fluoride compound, or combinations thereof, which has good stability, low toxicity to animal and plant life and high biocidal activity against wood decay fungi and termites. The composition additionally comprises organic fungicides and/or termiticides to further enhance the bio-efficacy.

The present invention also provides remedial paste compositions and methods for preservation of wooden poles, railroad ties and other wooden structures against both fungal and termite attack.

The invention also discloses a method for preparing a water-dilutable supplemental or remedial wood preserving composition which comprises milling the insoluble oxine copper compound in water.

The present invention provides a wood preservative composition comprising a copper-8-quinolinolate; a boron-containing compound; a carrier; and a thickening agent. In one embodiment, the carrier is non-aqueous or organic. In a preferred embodiment the carrier is aqueous. In a preferred embodiment, the composition is formulated as a paste. In a more preferred embodiment the composition is formulated as an aqueous paste. In the most preferred embodiment, the paste is thixotropic.

The wood preservative compositions of the present invention do not comprise one or more copper-solubilizing agents, such as ammonia, an ammonium salt, an amine, mono- or polyalkanolamines.

The wood preservative compositions of the present invention comprise copper-8-quinolinolate that is substantially insoluble in the carrier. In a preferred embodiment, the copper-8-quinolinolate is about 0.001% to about 10% by weight. In a more preferred embodiment, the copper-8-quinolinolate is about 0.001% to about 2% by weight. In the most preferred embodiment, the copper-8-quinolinolate is about 0.001% to about 1% by weight.

The boron-containing compound of the wood preservative compositions of the present invention are preferably boric acid, a metal borate, a sodium borate, or a potassium borate. In a preferred embodiment, the sodium borate is sodium tetraborate decahydrate, sodium tetraborate pentahydrate, or disodium octaborate tetrahydrate (DOT). The metal borate is preferably calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate or zinc borate. In one embodiment, the weight ratio of the boron compound to copper-8-quinolinolate is about 1:1. In a preferred embodiment, the weight ratio of the boron compound to copper-8-quinolinolate is about 10:1. In a more preferred embodiment, the weight ratio of the boron compound to copper-8-quinolinolate is about 200:1. In the most preferred embodiment, the weight ratio of the boron compound to copper-8-quinolinolate is about 1000:1.

The wood preservative compositions of the present invention may further comprise a fluoride-containing compound. In one embodiment, the fluoride compound is sodium fluoride, potassium fluoride, calcium fluoride, copper fluoride, iron fluoride, or magnesium fluoride. In one embodiment, the weight ratio of the fluoride compound to copper-8-quinolinolate is about 1:1. In a preferred embodiment, the weight ratio of the fluoride compound to copper-8-quinolinolate is about 10:1. In a more preferred embodiment, the weight ratio of the fluoride compound to copper-8-quinolinolate is about 200:1. In the most preferred embodiment, the weight ratio of the fluoride compound to copper-8-quinolinolate is about 1000:1.

The wood preservative compositions of the present invention may further comprise one or more organic biocides. The organic biocides suitable for use with the present invention may include a fungicide, insecticide, moldicide, bactericide, or algaecide, or combinations thereof. In another embodiment, the organic biocide is a quaternary ammonium compound, a triazole compound, an imidazole compound, an isothiazolone compound, or a pyrethroid compound, or combination thereof. In a preferred embodiment, the organic biocide is imidachloprid, fipronil, cyfluthrin, bifenthrin, permethrin, cypermethrin, chlorpyrifos, iodopropynyl butylcarbamate (IPBC), chlorothalonil, 2-(thiocyanatomethylthio) benzothiazole, alkoxylated diamines or carbendazim. In one embodiment, the weight ratio of the organic biocide is about from 0.001% to 10% by weight. In another embodiment, the weight ratio of the organic biocide is about from 0.005% to 5% by weight. In yet another embodiment, the weight ratio of the organic biocide is about from of 0.01% to 1% by weight.

The wood preservative compositions of the present invention are preferably formulated as pastes using an organic thickener, an inorganic thickener or a combination of organic and inorganic thickeners. In a preferred embodiment, the organic thickener is cellulose-derived, such as a cellulose ester or a cellulose ether. Preferably, the cellulose ester is cellulose nitrate, sulfate, cellulose phosphate, cellulose nitrite, cellulose xanthate, cellulose acetate, cellulose formate or combination thereof. Preferably, the cellulose ether is methylcellulose, ethylcellulose, propylcellulose, benzylcellulose, carboxymethylcellulose, hydroxyethylcellulose, hydroxypropylcellulose, hydroxybutylcellulose, cyanoethylcellulose, or carboxyethylcellulose. In one embodiment, the thickening agent is about 0.01% to 50% by weight in the composition. In another embodiment, the thickening agent is about 0.5% to 10% by weight in the composition.

In a preferred embodiment, the inorganic thickener of the wood preservative compositions of the present invention is a clay. Preferably, the clay is attapulgite, dickite, saponite, montmorillonite, nacrite, kaolinite, anorthite, halloysite, metahalloysite, chrysotile, lizardite, serpentine, antigorite, beidellite, stevensite, hectonite, smecnite, nacrite, sepiolite, montmorillonite, sauconite, stevensite, nontronite, saponite, hectorite, vermiculite, illite, sericite, glauconite-montmorillonite, roselite-montmorillonite, bentonite, chlorite-vermiculite, illite-montmorillonite, halloysite-montmorillonite, or kaolinitemontmorillonite. More preferably, the clay is attapulgite, hectorite, bentonite, montmorillonite, sauconite, smecnite, stevensite, beidellite, nontronite, saponite, hectorite, vermiculite, nacrite, or sepiolite. In one embodiment, the inorganic thickener is about 0.5% to about 30% by weight.

The wood preservative compositions of the present invention may also further comprise a drying retardant or a hemictant, or both.

The wood preservative composition of the present invention may be packaged in containers, wraps, bandages and the like. In one embodiment, the container is a can, a bucket or a bag. In one embodiment the compositions of the present invention packaged in a container have a viscosity between 175 and 375 tenths of a millimeter (tmm). In a preferred embodiment, the viscosity is between 200 and 300 tmm. In a more preferred embodiment, the viscosity is between 210 and 250 tmm.

The present invention also provides a method for remedial treatment of wood, comprising the step of applying the composition of the present invention to wood. In a preferred method, the wood is an in-service wood product, such as a utility pole, a railroad tie or wooden bridge. Preferably, the compositions of the present invention are applied by brush or spray. Preferably, the composition is applied to wood to a thickness of between 1/32 and 3/4 inches. In a more preferred embodiment, the composition is applied to wood to a thickness of between 1/16 and 1/2 inches. In a most preferred embodiment, the composition is applied to wood to a thickness of between 1/16 and 1/4 inches.

The present invention also provides a method for preparing the wood preservative composition of the present invention comprising the step of maintaining the viscosity of the wood preservative composition between 275 and 425 tenths of a millimeter (tmm). In a preferred embodiment, the viscosity is maintained between 300 and 400 tmm. In a more preferred embodiment, the viscosity is maintained between 320 and 340 tmm.

DETAILED DESCRIPTION OF THE INVENTION

Unless stated otherwise, such as in the examples, all amounts and numbers used in this specification are intended to be interpreted as modified by the term "about". Likewise, all elements or compounds identified in this specification, unless stated otherwise, are intended to be non-limiting and representative of other elements or compounds generally considered by those skilled in the art as being within the same family of elements or compounds.

As used herein, the term "micronized" means a particle size in the range of 0.001 to 25 microns. As used herein, the term "particle size" means the largest axis of the particle, and in the case of a generally spherical particle, the largest axis is the diameter. Furthermore, it should be understood that "micronized" does not refer only to particles which have been produced by the finely dividing, such as by mechanical grinding, of materials which are in bulk or other form. Micronized particles can also be formed by other mechanical, chemical or physical methods, such as, for example, formation in solution, with or without a seeding agent, grinding or impinging jet. The micronized copper particles disclosed in U.S. Publication No. 20050118280 are hereby specifically incorporated by reference, in their entirety.

As used herein, "copper-solubilizing agents" mean any agent that promotes the solubility of copper metal or a copper compound in an aqueous carrier. Copper-solubilizing agents include, but are not limited to ammonia and ammonium salts, amines, and alkanolmonoamines having between 2 to 18 carbon atoms, such as monoalkanolmonoamines, dialkanolmonoamines, and trialkanolmonoamines, and mixtures thereof. Examples include monoethanolamine, diethanolamine, triethanolamine, 3-aminopropanol, monoisopropanolamine, 4-aminobutanol, monomethylethanolamine, dimethylethanolamine, triethylethanolamine, monoethylethanolamine, N-methyldiethanolamine and mixtures thereof.

As used herein, "remedial treatment" means the treatment of wood previously treated with one or more wood preservatives.

Disclosed herein is a supplemental/remedial composition for wood and a method for use thereof in treatment of in-service wooden products, more particularly utility poles, railroad ties, wooden bridges. The composition comprises oxine copper with a boron compound or fluoride compound. The composition imparts to the treated wood resistance to both fungi and insects. The composition can additionally comprise an organic fungicide/termiticide.

The compositions of the present invention have a broad spectrum of bio-efficacy against wood decay fungi, including, brown rot fungi, white rot fungi, and soft rot fungi. Non-limiting examples of brown rot fungi include: *Coniophora puteana, Serpula lacrymans, Antrodia vaillantii, Gloeophyllum trabeum, Gleoeophyllum sepiarium, Lentinum lepideus, Oligoporus placenta, Meruliporia incrassate, Daedalea quercina, Postia placenta*. Non-limiting examples of white rot fungi include: *Trametes versicolor, Phanerochaete chrysosporium, Pleurotus ostreatus, Schizophyllum commune, Irpex lacteus*. Some non-limited examples of white rot fungi are *Chaetomium globosum, Lecythophora hoffmannii, Monodictys putredinis, Humicola alopallonella, Cephalosporium, Acremonium*, and *Chaetomium*.

The compositions of the present invention are also effective against a broad range of insects and marine borer, including termites, beetles, and wood-boring insects. Non-limiting examples of termites include drywood termites such as *Cryptotermes* and *Kaloterms*, and dampwood termites such as *Zootermopsis*, subterranean termites such as *Coptotermes, Mastotermes, Reticulitermes, Schedorhinotermes, Microcerotermes, Microtermes*, and *Nasutitermes*. Non-limiting examples of beetles include those in families such as, for example, *Anoniidae, Bostrychidae, Cerambycidae, Scolytidae, Curculionidae, Lymexylonidae*, and *Buprestidae*.

The compositions of the present invention can be formulated into a waterborne paste- or grease-type of formulation, if desired, such that the formulation has an adhesive nature and is easy to apply to a desired location.

The present invention includes oxine copper. The preferred form of oxine copper in the present invention is a fine particulate, such that is found in dispersions through the milling process. Methods for preparing milled substantially insoluble biocidal particulates that can effectively penetrate and preserve wood may be found in U.S. Pat. App. No.'s 20040258767, 20050118280 and 20060288904 to Leach and Zhang. Although it is not the most preferred, the current composition can also be formulated into an oil-borne paste- or grease-like formulation where the oxine copper is solubilized with an organic solvent.

The weight ratio of oxine copper in the composition varies from about 0.001% to about 10% by weight. The preferred range of weight ratio of oxine copper in the composition varies from about 0.01% to about 1% by weight.

The present invention also comprises a boron compound, a fluoride compound or both. The boron compound can be either water soluble or water insoluble. Non-limiting examples of water soluble boron compounds include boric acid, sodium borates, such as sodium tetraborate decahydrate, sodium tetraborate pentahydrate, and disodium octaborate tetrahydrate (DOT) and potassium borates. Non-limiting examples of water insoluble boron compounds include metal borate compounds such as calcium borate, borate silicate, aluminum silicate borate hydroxide, silicate borate hydroxide fluoride, hydroxide silicate borate, sodium silicate borate, calcium silicate borate, aluminum borate, boron oxide, magnesium borate, iron borate, copper borate and zinc borate.

Preferred boron compounds are water soluble boron compounds, such as boric acid and sodium tetraborate decahydrate, sodium tetraborate pentahydrate and disodium octaborate tetrahydrate (DOT).

The weight ratio of boron compound to oxine copper can be in the range of from about 1:1 to about 1000:1, the preferred weight ratio range is about 10:1 to about 200:1.

The present invention can also include a fluoride compound. Non-limiting examples of fluoride compounds include sodium fluoride, potassium fluoride, calcium fluoride, copper fluoride, iron fluoride, magnesium fluoride, and other metal compounds of fluoride. The preferred fluorides are sodium fluoride and potassium fluoride. The weight ratio of fluoride compound to oxine copper can be in the range of from about 1:1 to about 1000:1, the preferred weight ratio range is about 10:1 to about 200:1.

The present composition optionally comprises one or more combinations of a organic biocides, such as quaternary ammonium compounds, triazole or imidazole compounds, isothiazolone compounds, pyrethroid compounds and other biocides such as imidachloprid; fipronil; cyfluthrin; bifenthrin; permethrin; cypermethrin; and chlorpyrifos, iodopropynyl butylcarbamate (IPBC); chlorothalonil; 2-(thiocyanatomethylthio) benzothiazole; alkoxylated diamines and carbendazim. When the organic biocide is used in the composition, the weight ratio of the organic biocide in the composition is generally in the range of from 0.001% to 10% by weight, with a preferred range of 0.005% to 5% by weight and a more preferred range of 0.01% to 1%.

Each of the organic biocides listed in Tables 1-4 of U.S. Publication No. 20050118280 are hereby specifically incorporated by reference, in their entirety.

Non-limiting examples of quaternary ammonium compounds are: didecyldimethylammonium chloride; didecyldimethylammonium carbonate/bicarbonate; alkyldimethylbenzylammonium chloride; alkyldimethylbenzylammonium carbonate/bicarbonate; didodecyldimethylammonium chloride; didodecyldimethylammonium carbonate/bicarbonate; didodecyldimethylammonium propionate; N,N-didecyl-N-methyl-poly(oxyethyl) ammonium propionate.

Non-limiting examples of triazole or imidazole compounds are: 14[242,4-dichlorophenyl)-1,3-dioxolan-2-yl] methyl]-1H-1,2,4-triazole (azaconazole), 1 R2RS,4RS:2RS, 4SR)-4-bromo-2-(2,4-dichlorophenyptetrahydrofurfuryl]-1H-1,2,4-triazole (bromuconazole), (2RS,3RS;2RS,3SR)-2-(4-chlorophenyl)-3-cyclopropyl-1-(1H-1,2,4-triazol-1-yl) butan-2-ol (Cyproconazole), (2RS,3RS)-1-(2,4-dichlorophenyl)-4,4-dimethyl-2-(1H-1,2,4-triazol-1-yl) pentan-3-ol (diclobutrazol), cis-trans-3-chloro-444-methyl-2-(1H-1,2,4-triazol-1-ylmethyl)-1,3-dioxolan-2-yliphenyl 4-chlorophenyl ether (difenoconazole), (E)-(R5)-1-(2,4-dichlorophenyl)-4,4-dimethyl-2-(1H-1,2,4-triazol-1-yl) pent-1-en-3-ol (diniconazole), (E)-(R)-1-(2,4-dichlorophenyl)-4,4-dimethyl-2-(1H-1,2,4-triazol-1-yl)pent-1-en-3-ol (diniconazole-M), (2RS,3SR)-143-(2-chlorophenyl)-2,3-epoxy-2-(4-fluorophenyl)propyl]-1H-1,2,4-triazole (epoxiconazole), (RS)-142-(2,4-dichlorophenyl)-4-ethyl-1,3-dioxolan-2-ylmethyli-1H-1,2,4-triazole (etaconazole), (RS)-4-(4-chlorophenyl)-2-phenyl-2-(1H-1,2,4-triazol-1-ylmethyl) butyronitrile (fenbuconazole), 3-(2,4-dichlorophenyl)-6-fluoro-2-(1H-1,2,4-triazol-1-yl)quinazolin-4(311)-one (fluquinconazole), bis(4-fluorophenyl)(methyl)(1H-1,2,4-triazol-1-ylmethyl)silane (flusilazole), (RS)-2,4'-difluoro-a-(1H-1,2,4-triazol-1-ylmethyl)benzhydryl alcohol (flutriafol), (2RS,5RS,2RS,5SR)-5-(2,4-dichlorophenyl)tetrahydro-5-(1H-1,2,4-triazol-1-ylmethyl)-2-furyl 2,2,2-trifluoroethyl ether (furconazole), (2RS,5RS)-5-(2,4-dichlorophenyptetrahydro-54 1H-1,2,4-triazol-1-ylmethyl)-2-furyl 2,2,2-trifluoroethyl ether(furconazole-cis), (RS)-2-(2,4-dichlorophenyl)-1-(1H-1,2,4-triazol-1-yl)hexan-2-ol (hexaconazole), 4-chlorobenzyl (EZ)-N-(2,4-dichlorophenyl)-2-(1H-1,2,4-triazol-1-yl)thioacetamidate (imibenconazole),_(1RS,2SR, 5RS;1RS,2SR,5SR)-2-(4-chlorobenzyl)-5-isopropyl-1-(1H-1,2,4-triazol-1-ylmethyl)cyclopentanol (ipconazole), (1RS, 5RS;1RS,5SR)-5-(4-chlorobenzyl)-2,2-dimethyl-1-(1H-1,2, 4-triazol-1-ylmethyl)cyclopentanol (metconazole), (RS)-2-(4-chlorophenyl)-24 1H-1,2,4-triazol-1-ylmethyl) hexanenitrile (myclobutanil), (RS)-1-(2,4-dichloro-(3-propylphenethyl)-1H-1,2,4-triazole(penconazole), cis-trans-1-[2-(2,4-dichlorophenyl)-4-propyl-1,3-dioxolan-2-ylmethyl]-1H-1,2,4-triazole (propiconazole), (RS)-2-[2-(1-chlorocyclopropyl)-3-(2-chlorophenyl)-2-hydroxypropyll-2,4-dihydro-1,2,4-triazole-3-thione(prothioconazole), 3-(2, 4-dichlorophenyl)-2-(1H-1,2,4-triazol-1-yl)-quinazolin-4 (311)-one (quinconazole), (RS)-2-(4-fluorophenyl)-1-(1H-1, 2,4-triazol-1-yl)-3-(trimethylsilyl)propan-2-ol (simeconazole), (RS)-1-p-chlorophenyl-4,4-dimethyl-3-(1H-1,2,4-triazol-1-ylmethyl)pentan-3-ol (tebuconazole), propiconazole, (RS)-2-(2,4-dichlorophenyl)-3-(1H-1,2,4-triazol-1-yl)propyl 1,1,2,2-tetrafluoroethyl ether (tetraconazole), (RS)-1-(4-chlorophenoxy)-3,3-dimethyl-1-(1H-1,2,4-triazol-1-yl)butan-2-one (triadimefon), (1RS,2RS;1RS, 2SR)-1-(4-chlorophenoxy)-3,3-dimethyl-1-(1H-1,2,4-triazol-1-yl)butan-2-ol (triadimenol), (RS)-(E)-5-(4-chlorobenzylidene)-2,2-dimethyl-1-(1H-1,2,4-triazol-1-ylmethyl)cyclopentanol (triticonazole), (E)-(RS)-1-(4-chlorophenyl)-4,4-dimethyl-2-(1H-1,2,4-triazol-1-yl)pent-1-en-3-ol (uniconazole), (E)-(S)-1-(4-chlorophenyl)-4,4-dimethyl-24 1H-1,2,4-triazol-1-yl)pent-1-en-3-ol (uniconazole-P), and 2-(2,4-difluorophenyl)-1-(1H-1,2,4-triazole-1-yl)-3-trimethylsilyl-2-propanol. Other azole compounds include: amisulbrom, bitertanol, fluotrimazole, triazbutil, climbazole, clotrimazole, imazalil, oxpoconazole, prochloraz, triflumizole, azaconazole, simeconazole, and hexaconazole.

Non-limiting examples of isothiazolone compounds are: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothiazolinone; 4,5-Dichloro-2-n-octyl-3(2H)-isothiazolone; 1,2-benzisothiazolin-3-one.

Non-limiting examples of pyrethroid compounds include acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen.

Preferred organic biocides are tebuconazole and bifenthrin.

The present invention also optionally comprises an aqueous type thickening agent. Aqueous organic polymer, aqueous emulsion, clay minerals, phosphate and the like are the aqueous type of thickening agents. Typical examples of aqueous organic polymers are cellulose derivatives including cellulose esters and ethers. Examples of cellulose esters are cellulose nitrate, sulfate, cellulose phosphate, cellulose nitrite, cellulose xanthate, cellulose acetate, cellulose formate, and cellulose esters with other organic acids. Examples of cellulose ethers are methylcellulose, ethylcellulose, propylcellulose, benzylcellulose, carboxymethylcellulose, hydroxyethylcellulose, hydroxypropylcellulose, hydroxybutylcellulose, cyanoethylcellulose, and carboxyethylcellulose. The preferred cellulose derivatives are cellulose ethers such as hydroxyethylcellulose, hydroxypropylcellulose, carboxymethylcellulose and carboxyethylcellulose. The weight percentage of the cellulose derivative in the paste formulation is generally in the range of from about 0.01% to 50% with a preferred weight percentage of 0.1 to 20% and a more preferred weight percentage of 0.5 to 10%.

Furthermore, the present invention also optionally comprises about 0.5% to about 30% of an inorganic clay thickening agent, or a mixture of such thickening agents. The inorganic clay thickening agents include a fibrous structure type such as attapulgite clay and sepiolite clay, a non-crystal structure type such as allophone, and mixed layer structure type such as montmorillonite and kaolinte and the above layer structure types. Examples of inorganic clay minerals, but not limited to, are: attapulgite, dickite, saponite, montmorillonite, nacrite, kaolinite, anorthite, halloysite, metahalloysite, chrysotile, lizardite, serpentine, antigorite, beidellite, stevensite, hectonite, smecnite, nacrite and sepiolite, montmorillonite, sauconite, stevensite, nontronite, saponite, hectorite, vermiculite, smecnite, sepiolite, nacrite, illite, sericite, glauconite-montmorillonite, roselite-montmorillonite, Bentone 38 (hectorite) and Bentone 34 (bentonite), chlorite-vermiculite, illite-montmorillonite, halloysite-montmorillonite, kaolinitemontmorillonite. The clay minerals employed in the compositions of the present invention also contain exchangeable cations including, but not limited to, aluminum ions, protons, sodium ions, potassium ions, calcium ions, magnesium ions, lithium ions, and the like.

Among the above inorganic clay minerals, attapulgite, hectorite, bentonite, montmorillonite, sauconite, smecnite, stevensite, beidellite, nontronite, saponite, hectorite, vermiculite, nacrite, and sepiolite are particularly preferable for the present invention.

Further, these inorganic clay minerals show a good thickening effect and thixotopic property in comparison with other aqueous thickening agents. Therefore, they show a little sagging and also they are very easy to be rinsed out by water in comparison with organic thickening agents.

It should be appreciated that thickening agents other than described herein can be used.

Optionally, the present invention also includes chemical additives that retard the drying of the paste composition. These are usually a blend of several glycols, such as ethylene glycol, propylene glycol, polyethylene glycol, polypropylene glycol and their derivatives. By evaporating far more slowly than water, glycols or their derivatives can slow down the drying process of the paste composition. Humectants, such as glycerin and glycerol that absorb or hold water can also be added to retard or slow drying.

The preservative paste compositions of this invention can be applied by various processes of supplemental or remedial treatment or protection of in-service wooden structures. The compositions of this invention are suitable for incorporation into wraps or ready-to-use bandages, injection into voids or cavities by pressure or by gravity and solid rods or cartridges.

The paste compositions of this invention can be easily incorporated into a suitable support material to form a ready-to-use bandage or wrap that can applied to in-service utility poles and other wooden structures. Numerous support materials have been identified in literature and may include polymer films, fabrics, fiberglass, polyester fiber, polypropylene, porous polymer compositions and others that allow for the transfer or diffusion of preservative chemical from the bandage to the wood substrate. The paste composition may be applied to the support material by toweling, rolling, brushing and the like. The paste composition can be directly applied to the support material or may require the use of a binder or resin such as for example acrylate resins or PVC with plasticizers. To improve the adhesion between the paste compositions and support material the combination may be air-dried or dried in an oven at elevated temperatures.

The paste compositions of this invention may also be formed into solid rods by extrusion, rolling or pressing. Once sufficiently dried, the rods can be cut to length and inserted into predrilled holes in in-service utility poles or other wooden structures. As with the bandages or wraps, resins or binders may be added to improve the dimensional stability of the rods.

The paste compositions of this invention may be injected into internal voids or cavities through predrilled holes into in-service poles, posts, piling, cross-ties and other wooden structures by pressure processes or by gravity feed.

The following examples are provided to further describe certain embodiments of the invention, their preparation and application as remedial or supplemental paste preserving system, but are in no way meant to limit the scope of the invention. For the experiments, penetration testing has been found to be an effective means of establishing the consistency and shear stability of compositions of this invention. Penetrometers are generally used for consistency tests on a wide range of food products, cosmetics, greases, pastes and other solid to semisolid products. Penetrometers utilize a standard cone or needle that is released from the Penetrometer and allowed to drop feely into the sample for 5 seconds at constant temperature. The depth of penetration of the cone into the sample is measured in tenths of a millimeter (tmm) by the Penetrometer. It has been establish through testing that the preferable penetration of the compositions of this invention range from about 125 to 425 tmm when using a standard Penetrometer quipped with a 102.5 gram brass cone with a stainless steel tip. A more preferable range of consistency for the present invention is about 175 to 375 tmm and a consistency or shear stability of about 200 to 300 tmm is particularly preferable for the present invention.

The preferred viscosities of the thixotropic compositions of the present invention, during manufacture, is between 275 and 425 tenths of a millimeter (tmm) viscosity as measured using a penetrometer. More preferably the viscosities of the compositions of the present invention is between 300 and 400 tmm. Most preferably the viscosities of the compositions of the present invention is between 320 and 340 tmm.

The preferred viscosities of the thixotropic compositions of the present invention is between 175 and 375 tenths of a millimeter (tmm) viscosity as measured using a penetrometer. More preferably the viscosities of the compositions of the present invention is between 200 and 300 tmm. Most preferably the viscosities of the compositions of the present invention is between 210 and 250 tmm.

For determination of acceptability of viscosity, spreadability and adherence, compositions of the present invention can be rolled, troweled or brushed on wooden objects or more preferably to in-service utility poles, cross-ties or other wooden structures. Desirable compositions of the present invention should be self-supporting, have good spreadability such that the composition can be easily applied with a roller, trowel or brush without running or slumping off the wooden substrate or application tool and will easily adhere to a wooden substrate.

EXAMPLE 1

A supplemental/remedial preservative paste composition was prepared by blending together in the order listed; 44.92 parts water, 0.88 parts of a fine oxine copper dispersion comprised of 34.18% oxine copper, 2.00 parts of a commercially available cellulose ether thickener, 43.7 parts sodium tetraborate decahydrate, 1.0 part calcium sulfate filler and 7.5 parts attapulgite clay thickener. This remedial preservative paste contained 0.30 parts oxine copper as derived from the fine oxine copper dispersion for a weight ratio of 145.67 parts boron compound to 1.00 part oxine copper.

The supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

EXAMPLE 2

A supplemental/remedial preservative paste composition was prepared by blending together in the order listed; 34.74 parts water, 0.10 antifoam, 1.46 parts of a fine oxine copper dispersion comprised of 34.18% oxine copper, 10.00 parts glycerin, 2.00 parts of a commercially available cellulose ether thickener, 43.70 parts sodium tetraborate decahydrate, 1.00 part calcium sulfate filler and 7.0 parts attapulgite clay thickener. This remedial preservative paste contained 0.50 parts oxine copper as derived from the fine oxine copper dispersion for a weight ratio of 87.40 parts boron compound to 1.00 part oxine copper.

The supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

EXAMPLE 3

A supplemental/remedial preservative paste composition was prepared by blending together in the order listed; 30.24 parts water, 0.10 antifoam, 4.00 parts wax emulsion, 1.46 parts of a fine oxine copper dispersion comprised of 34.18% oxine copper, 10.00 parts glycerin, 3.00 parts of a commercially available cellulose ether thickener, 43.70 parts sodium tetraborate decahydrate, 1.50 part calcium sulfate filler and 6.0 parts attapulgite clay thickener. This remedial preservative paste contained 0.50 parts oxine copper as derived from the fine oxine copper dispersion for a weight ratio of 87.40 parts boron compound to 1.00 part oxine copper.

The supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

EXAMPLE 4

A supplemental/remedial preservative paste composition is prepared by blending together in the order listed; 30.22 parts water, 0.10 antifoam, 0.02 parts bifenthrin, 4.00 parts wax emulsion, 1.46 parts of a fine oxine copper dispersion comprised of 34.18% oxine copper, 10.00 parts propylene glycol, 3.00 parts of a commercially available cellulose ether thickener, 43.70 parts sodium tetraborate decahydrate, 1.50 part calcium sulfate filler and 6.0 parts attapulgite clay thickener.

This remedial preservative paste contains 0.50 parts oxine copper as derived from the fine oxine copper dispersion for a weight ratio of 87.40 parts boron compound to 1.00 part oxine copper.

EXAMPLE 5

A supplemental/remedial preservative paste composition is prepared by blending together in the order listed; 29.41 parts water, 0.10 antifoam, 0.10 parts tebuconazole, 4.00 parts wax emulsion, 2.19 parts of a fine oxine copper dispersion comprised of 34.18% oxine copper, 10.00 parts glycerin, 3.00 parts of a commercially available cellulose ether thickener, 21.85 parts sodium tetraborate decahydrate, 21.85 parts boric acid, 1.50 part calcium sulfate filler and 6.0 parts attapulgite clay thickener.

This remedial preservative paste contains 0.75 parts oxine copper as derived from the fine oxine copper dispersion for a weight ratio of 58.27 parts boron compound to 1.00 part oxine copper.

EXAMPLE 6

A supplemental/remedial preservative paste composition was prepared by blending together in the order listed; 34.30 parts water, 10.00 parts glycerin, 2.00 parts of a commercially available cellulose ether thickener, 0.88 parts of a fine oxine copper dispersion comprised of 35.80% oxine copper, 0.02 parts bifenthrin, 2.00 parts wax emulsion, 0.10 parts tebuconazole, 43.70 parts sodium tetraborate decahydrate, 5.5 parts attapulgite clay thickener and 1.5 parts calcium sulfate filler. This remedial preservative paste contained 0.32 parts oxine copper as derived from the fine oxine copper dispersion for a weight ratio of 136.56 parts boron compound to 1.00 part oxine copper.

Penetration testing performed on the paste composition formulated according to the example above showed a penetration of 210 tmm. In addition, the supplemental/remedial preservative paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

Further, the paste formed was applied to the surface of southern pine dimensional lumber that had previously been vacuum-pressure impregnated with water. The lumber was saturated with water to simulate moisture regimes that are typically present within the ground-line region of in-service utility poles and other wooden structures and that is required to provide mobility of the preservative paste into the wood substrate. The paste was applied at a thickness of a sixteenth of an inch and sealed to the lumber with a water impermeable wrap such that is used in commercial practice. At periods of 2, 4 and 6 weeks, small incremental wafers were taken from the treated sections of the lumber. It was determined by analytical testing that oxine copper had penetrated, or diffused through the wood at fungitoxic levels up to a i/2 inch from the surface of application. It was further determined that fungitoxic levels of boron had penetrated the wood up to 1-V2 inches from the treated surface.

EXAMPLE 7

A supplemental/remedial preservative paste composition was prepared by blending together in the order listed; 31.90 parts water, 0.10 parts antifoam, 0.20 parts tebuconazole, 0.04 parts bifenthrin, 4.00 parts wax emulsion, 0.84 parts of a fine oxine copper dispersion comprised of 35.80% oxine copper, 10.00 parts glycerin, 2.00 parts of a commercially available cellulose ether thickener, 43.70 parts sodium tetraborate decahydrate, 1.22 parts calcium sulfate filler and 6.00 parts attapulgite clay thickener. This remedial preservative paste contained 0.30 parts oxine copper as derived from the fine oxine copper dispersion for a weight ratio of 145.67 parts boron compound to 1.00 part oxine copper.

Penetration testing performed on the paste composition formulated according to the example above showed a penetration of 291 tmm. Further, the paste composition formulated according to the above example was brushed to 18 inches of the below ground section of an in-service utility pole by an experienced preservative chemical applicator. This paste was found to have desirable physical properties including viscosity, spreadability and adherence for application to in-service utility poles, cross-ties and other wooden structures. Consequently, a preservative paste composition was obtained.

EXAMPLE 8

A supplemental/remedial preservative paste composition was prepared by blending together in the order listed; 31.17 parts water, 0.10 parts antifoam, 0.20 parts tebuconazole, 0.04 parts bifenthrin, 3.98 parts wax emulsion, 1.39 parts of a fine oxine copper dispersion comprised of 35.80% oxine copper, 9.94 parts glycerin, 1.99 parts of a commercially available cellulose ether thickener, 43.46 parts sodium tetraborate decahydrate, 1.21 parts calcium sulfate filler and 6.52 parts attapulgite clay thickener. This remedial preservative paste contained 0.50 parts oxine copper as derived from the fine oxine copper dispersion for a weight ratio of 86.92 parts boron compound to 1.00 part oxine copper.

Penetration testing performed on the paste composition formulated according to the example above showed a penetration of 239 tmm. Further, the paste composition formulated according to the above example was brushed to 18 inches of the below ground section of an in-service utility pole by an experienced preservative chemical applicator. This paste was found to have desirable physical properties including viscosity, spreadability and adherence for application to in-service utility poles, cross-ties and other wooden structures. Consequently, a preservative paste composition was obtained.

EXAMPLE 9

A supplemental/remedial preservative paste composition was prepared by blending together in the order listed; 31.40 parts water, 0.10 parts antifoam, 0.20 parts tebuconazole, 0.04 parts bifenthrin, 4.00 parts wax emulsion, 0.84 parts of a fine oxine copper dispersion comprised of 35.80% oxine copper, 10.00 parts glycerin, 2.00 parts of a commercially available cellulose ether thickener, 43.70 parts sodium tetraborate decahydrate, 1.22 parts calcium sulfate filler and 6.50 parts attapulgite clay thickener. This remedial preservative paste contained 0.30 parts oxine copper as derived from the fine oxine copper dispersion for a weight ratio of 145.67 parts boron compound to 1.00 part oxine copper.

Penetration testing performed on the paste composition formulated according to the example above showed a penetration of 232 tmm. Further, the paste composition formulated according to the above example was brushed to 18 inches of the below ground section of an in-service utility pole by an experienced preservative chemical applicator. This paste was found to have desirable physical properties including viscosity, spreadability and adherence for application to in-service utility poles, cross-ties and other wooden structures. Consequently, a preservative paste composition was obtained.

EXAMPLE 10

A supplemental/remedial preservative paste composition is prepared by blending together in the order listed; 31.90 parts water, 0.10 parts antifoam, 0.20 parts tebuconazole, 0.04 parts bifenthrin, 4.00 parts wax emulsion, 0.84 parts of a fine oxine copper dispersion comprised of 35.80% oxine copper, 10.00 parts glycerin, 2.00 parts of a commercially available cellulose ether thickener, 21.85 parts sodium tetraborate decahydrate, 21.85 parts sodium fluoride, 1.22 parts calcium sulfate filler and 6.00 parts attapulgite clay thickener.

This remedial preservative paste contains 0.30 parts oxine copper as derived from the fine oxine copper dispersion for a weight ratio of 72.83 parts boron compound to 1.00 part oxine copper and 72.83 parts fluoride compound to 1.00 part oxine copper.

EXAMPLE 11

A supplemental/remedial preservative paste composition is prepared by blending together in the order listed; 31.90 parts water, 0.10 parts antifoam, 0.20 parts tebuconazole, 0.04 parts bifenthrin, 4.00 parts wax emulsion, 0.84 parts of a fine oxine copper dispersion comprised of 35.80% oxine copper, 10.00 parts glycerin, 2.00 parts of a commercially available cellulose ether thickener, 43.70 parts sodium fluoride, 1.22 parts calcium sulfate filler and 6.00 parts attapulgite clay thickener.

This remedial preservative paste contains 0.30 parts oxine copper as derived from the fine oxine copper dispersion for a weight ratio of 145.67 parts fluoride compound to 1.00 part oxine copper.

EXAMPLE 12

A supplemental/remedial preservative paste composition is prepared by blending together in the order listed; 31.64 parts water, 0.10 parts antifoam, 4.00 parts wax emulsion, 0.84 parts of a fine oxine copper dispersion comprised of 35.80% oxine copper, 10.00 parts glycerin, 2.00 parts of a commercially available cellulose ether thickener, 43.70 parts boric acid, 1.22 parts calcium sulfate filler and 6.50 parts attapulgite clay thickener.

This remedial preservative paste contains 0.30 parts oxine copper as derived from the fine oxine copper dispersion for a weight ratio of 145.67 parts boron compound to 1.00 part oxine copper.

EXAMPLE 13

A supplemental/remedial preservative paste composition is prepared by blending together in the order listed; 41.79 parts water, 10.00 parts propylene glycol, 0.88 parts of a fine oxine copper dispersion comprised of 34.18% oxine copper, 0.33 parts didecyldimethylammonium carbonate/bicarbonate, 2.00 parts of a commercially available cellulose ether thickener, 36.0 parts disodium octaborate tetrahydrate, 2.0 part calcium sulfate filler and 7.0 parts attapulgite clay thickener.

This remedial preservative paste contains 0.30 parts oxine copper as derived from the fine oxine copper dispersion for a weight ratio of 120.00 parts boron compound to 1.00 part oxine copper.

EXAMPLE 14

The supplemental/remedial preservative paste composition of Example 7 was continuously extruded through a ⅜ inch diameter aperture and subsequently cut into 3 inch lengths. The rods were then dried at 90° F. for 24 hours. The resulting preservative rods were found to be structurally sound, uniformly shaped and preferable for insertion into predrilled holes such that are drilled into in-service utility poles, piling, cross-ties and other wooden structures for the afterprotection against wood destroying decay fungi. Further, the rods were placed on a wet sponge partially submerged in a water bath to allow continual wicking of water from the bath to the rod. After six weeks it was determined through analysis that the water bath contained appreciable levels of oxine copper and boron. Consequently, a preservative rod composition was achieved.

EXAMPLE 15

The supplemental/remedial preservative paste composition of Example 7 was injected into ⅜ inch holes drilled into an in-service utility pole containing a large decay void. The preservative paste formulation was found to be easily pumped or transferred with standard pneumatic pumping equipment or by gravity feed. The pole section containing the void was subsequently dissected and the paste composition was found to have completely filled the void and achieved intimate contact with the surfaces of the wood such that would provide adequate diffusion of biocide to the wood substrate in the presence of moisture or liquid water. Consequently, a preservative internal treatment composition was achieved.

EXAMPLE 16

The supplemental/remedial preservative paste composition of Example 7 was rolled onto a polyethylene sheet to a uniform thickness of 0.0625 inches. The subsequent paste/support system was cut to 21 inches in length and applied to the below ground portion of an in-service utility pole such that the entire circumference of the pole was incased to 18 inches below ground. As the paste/support system was handled and transported the paste did not slump, run or drip off of the supporting material. Removal of the paste/support system from the pole shortly after application found that the paste composition adhered and maintained intimate contact with to the pole surface such that would provide adequate diffusion of the biocide to the wood substrate in the presence of moisture or liquid water. Consequently, a preservative wrap or bandage composition was achieved.

EXAMPLE 17

A supplemental/remedial preservative paste composition was prepared by blending together in the order listed; 38.75 parts No. 2 fuel oil, 1.25 parts oxine copper, 46.00 parts sodium fluoride, 10.00 part calcium sulfate filler, 3.00 parts bentonite clay thickener, 0.95 parts ethanol and 0.05 parts water. This remedial preservative paste contained 1.25 parts oxine copper for a weight ratio of 36.80 parts fluoride compound to 1.00 part oxine copper.

Penetration testing performed on the paste composition formulated according to the example above showed a penetration of 242 mm. Further, the paste composition formulated according to the above example was applied to a wooden substrate using a trowel and was found to have desirable physical properties including viscosity, spreadability and adherence for application to in-service utility poles, cross-ties and other wooden structures. Consequently, a preservative paste composition was obtained.

We claim:

1. A wood preservative composition comprising: copper-8-quinolinolate; a boron-containing compound; a carrier; and a thickening agent, wherein the copper-8-quinolinolate is present in an amount of about 0.001% to about 10% by weight of the composition, and wherein the composition is formulated as a paste having a viscosity of between 125 and 425 tenths of a millimeter (tmm) as measured using a penetrometer.

2. The wood preservative composition of claim 1, wherein the carrier is aqueous.

3. The wood preservative composition of claim 1, wherein the paste is thixotropic.

4. The wood preservative composition of claim 1, wherein the wood preservative composition does not comprise one or more copper-solubilizing agents.

5. The wood preservative composition of claim 4, wherein the copper-solubilizing agent comprises ammonia, an ammonium salt, an amine, mono- or polyalkanolamines.

6. The wood preservative composition of claim 1, wherein the copper-8-quinolinolate is substantially insoluble in the carrier.

7. The wood preservative composition of claim 1, wherein the copper-8-quinolinolate is present in an amount of about 0.001% to about 2% by weight of the composition.

8. The wood preservative composition of claim 7, wherein the copper-8-quinolinolate is present in an amount of about 0.001% to about 1% by weight of the composition.

9. The wood preservative composition of claim 1, wherein the boron-containing compound is a boric acid, a metal borate, a sodium borate, or a potassium borate.

10. The wood preservative composition of claim 9, wherein the sodium borate is sodium tetraborate decahydrate, sodium tetraborate pentahydrate, or disodium octaborate tetrahydrate (DOT).

11. The wood preservative composition of claim 1, wherein the weight ratio of the boron-containing compound to copper-8-quinolinolate is about 1:1.

12. The wood preservative composition of claim 1, wherein the weight ratio of the boron-containing compound to copper-8-quinolinolate is about 10:1.

13. The wood preservative composition of claim 1, wherein the weight ratio of the boron-containing compound to copper-8-quinolinolate is about 200:1.

14. The wood preservative composition of claim 1, wherein the weight ratio of the boron-containing compound to copper-8-quinolinolate is about 1000:1.

15. The wood preservative composition of claim 1, further comprising one or more organic biocides.

16. The wood preservative composition of claim 15, wherein the organic biocide is a fungicide, an insecticide, a moldicide, a bactericide, an algaecide, or a combination thereof.

17. The wood preservative composition of claim 15, wherein the organic biocide is a quaternary ammonium compound, a triazole compound, an imidazole compound, an isothiazolone compound, a pyrethroid compound, or a combination thereof.

18. The wood preservative composition of claim 15, wherein the organic biocide is imidachloprid, fipronil, cyfluthrin, bifenthrin, permethrin, cypermethrin, chlorpyrifos, iodopropynyl butyl carbamate (IPBC), chlorothalonil, 2-(thiocyanatomethylthio) benzothiazole, an alkoxylated diamine, or carbendazim.

19. The wood preservative composition of claim 15, wherein the organic biocide is present in an amount of about 0.001% to about 10% by weight of the composition.

20. The wood preservative composition of claim 19, wherein the organic biocide is present in an amount of about 0.005% to about 5% by weight of the composition.

21. The wood preservative composition of claim 20, wherein the organic biocide is present in an amount of about of 0.01% to about 1% by weight of the composition.

22. The wood preservative composition of claim 1, wherein the thickening agent is an organic thickener.

23. The wood preservative composition of claim 22, wherein the organic thickener is cellulose-derived.

24. The wood preservative composition of claim 23, wherein the cellulose-derived organic thickener is a cellulose ester or a cellulose ether.

25. The wood preservative composition of claim 23, wherein the organic thickener is cellulose nitrate, sulfate, cellulose phosphate, cellulose nitrite, cellulose xanthate, cellulose acetate, cellulose formate or a combination thereof.

26. The wood preservative composition of claim 24, wherein the cellulose ether is methylcellulose, ethylcellulose, propylcellulose, benzylcellulose, carboxymethylcellulose, hydroxyethyl cellulose, hydroxypropylcellulose, hydroxybutylcellulose, cyanoethylcellulose, or carboxyethylcellulose.

27. The wood preservative composition of claim 1, wherein the thickening agent is present in an amount of about 0.01% to about 50% by weight of the composition.

28. The wood preservative composition of claim 1, wherein the thickening agent is present in an amount of about 0.5% to about 10% by weight of the composition.

29. The wood preservative composition of claim 1, wherein the thickening agent is an inorganic thickener.

30. The wood preservative composition of claim 29, wherein the inorganic thickener is a clay.

31. The wood preservative composition of claim 30, wherein the clay is attapulgite, dickite, saponite, montmorillonite, nacrite, kaolinite, anorthite, halloysite, metahalloysite, chrysotile, lizardite, serpentine, antigorite, beidellite, stevensite, hectonite, smecnite, sepiolite, sauconite, nontronite, hectorite, vermiculite, illite, sericite, glauconite-montmorillonite, roselite-montmorillonite, bentonite, chlorite-vermiculite, illite-montmorillonite, halloysite-montmorillonite, or kaolinitemontmorillonite.

32. The wood preservative composition of claim 31, wherein the clay is attapulgite, hectorite, bentonite, montmorillonite, sauconite, smecnite, stevensite, beidellite, nontronite, saponite, vermiculite, nacrite, or sepiolite.

33. The wood preservative composition of claim 29, wherein the inorganic thickener is present in an amount of about 0.5% to about 30% by weight of the composition.

34. The wood preservative composition of claim 1, further comprising a drying retardant or a hemictant, or both.

35. The wood preservative composition of claim 1, wherein the thickening agent is a mixture of organic and inorganic thickeners.

36. The wood preservative composition of claim 1, further comprising a wrap.

37. The wood preservative composition of claim 36, wherein the wrap is a bandage.

38. A method for remedial treatment of wood, comprising the step of applying the composition of claim 1 to wood.

39. The method of claim 38, wherein the wood is an in-service wood product.

40. The method of claim 39, wherein the in-service wood product is a utility pole, a railroad tie or a wooden bridge.

41. The method of claim 38, wherein the composition is applied by brush.

42. The method of claim 38, wherein the composition is applied by spray.

43. The method of claim 38, wherein the composition is applied to wood to a thickness of between $\frac{1}{32}$ and $\frac{3}{4}$ inch.

44. The method of claim 38, wherein the composition is applied to wood to a thickness of between $\frac{1}{16}$ and $\frac{1}{12}$ inch.

45. The method of claim 38, wherein the composition is applied to wood to a thickness of between $\frac{1}{16}$ and $\frac{1}{4}$ inch.

46. A method for preparing the wood preservative composition of claim 1, comprising the step of maintaining the viscosity of the wood preservative composition at between 275 and 425 tmm.

47. The method of claim 46, wherein the viscosity is maintained at between 300 and 400 tmm.

48. The method of claim 47, wherein the viscosity is maintained at between 320 and 340 tmm.

49. A container comprising the wood preservative composition of claim 1.

50. The container of claim 49, wherein the container is a bag.

51. The container of claim 50, wherein the viscosity of the wood preservative composition is between 175 and 375 tmm.

52. The container of claim 51, wherein the viscosity is between 200 and 300 tmm.

53. The container of claim 52, wherein the viscosity is between 210 and 250 μm.

* * * * *